United States Patent
Makihara

[11] Patent Number: 6,149,621
[45] Date of Patent: Nov. 21, 2000

[54] IRRIGATION-ASPIRATION APPARATUS

[75] Inventor: Kiyoshi Makihara, Aichi, Japan

[73] Assignee: Nidek Co., Ltd., Aichi, Japan

[21] Appl. No.: 08/979,557

[22] Filed: Nov. 26, 1997

[30] Foreign Application Priority Data

Nov. 29, 1996 [JP] Japan ................. 8-334593

[51] Int. Cl.⁷ ............... A61M 1/00; F04B 43/08
[52] U.S. Cl. ........................... 604/27; 417/477
[58] Field of Search ............... 604/27, 30–32, 604/34, 35, 22, 80, 81, 118, 119, 50; 606/107; 417/477.1, 477.3, 477.8, 477.9, 477.11

[56] References Cited

U.S. PATENT DOCUMENTS

| | | | |
|---|---|---|---|
| 4,025,241 | 5/1977 | Clemens | 417/477 |
| 4,155,362 | 5/1979 | Jess | 417/477 |
| 4,921,477 | 5/1990 | Davis. | |
| 4,969,808 | 11/1990 | Tsukada | 417/477 |
| 5,062,775 | 11/1991 | Orth | 417/477 |
| 5,230,614 | 7/1993 | Zanger et al. | |
| 5,810,765 | 9/1998 | Oda | 604/31 |

FOREIGN PATENT DOCUMENTS

| | | |
|---|---|---|
| 52-52466 | 11/1977 | Japan. |
| 5-520076 | 5/1980 | Japan. |
| 55-160190 | 12/1980 | Japan. |

*Primary Examiner*—Sharon Kennedy
*Attorney, Agent, or Firm*—Sughrue, Mion, Zinn, Macpeak & Seas, PLLC

[57] ABSTRACT

An irrigating fluid from irrigating bottle (10) is supplied to the eye under operation through the tip of US handpiece (2) and sucked in through flexible aspirating tube (16) together with the residue in the eye. Peristaltic pump (20) sucks in the liquefied residue in the eye by means of rollers (21) which compress the aspirating tube (16) to collapse as they rotate. Block (28) is provided just prior to the point where the rollers (21) start compressing the aspirating tube (16) to collapse, such that the aspirating tube (16) is flattened while securing the aspirating path in the tube (16) as it is held between the block (28) and tube receptacle (25). The change in the capacity of the aspirating tube (16) which occurs when the rollers (21) compress the aspirating tube (16) is limited so that only a small volume of the liquefied residue will flow back. Thus, it is possible to reduce the pulsation from aspiration, thereby ensuring consistent rate of inflow.

15 Claims, 4 Drawing Sheets

6,149,621

IRRIGATION-ASPIRATION APPARATUS

BACKGROUND OF THE INVENTION

The present invention relates to an irrigation-aspiration apparatus for typical use in cataract surgery which involves the extraction of an opaque lens due to cataract.

An irrigation-aspiration apparatus is known that supplies an irrigating fluid into the eyeball and which removes through aspiration the supplied irrigating fluid together with the tissue to be stripped from within the eyeball. This apparatus is typically used in cataract surgery which involves the extraction of an opaque lens due to cataract. Primarily for the reason of creating only a small incision wound, an ultrasonic phacoemulsification and aspiration technique using a spallation handpiece which operates under ultrasonic vibrations (hereunder referred to as an "US handpiece") is commonly practiced today in cataract surgery.

In this method of surgery, ultrasonic vibrations are applied to the tubular spallation tip having an aspiration hole at the distal end of the US handpiece so as to spall and emulsify the nucleus in the lens. During the operation, an irrigating fluid flowing through an irrigation tube is supplied into the eyeball from a site near the distal end of the spallation tip. The nuclei spalled and emulsified in smaller particles by the ultrasonic vibrations applied to the spallation tip is given an aspirating pressure by the aspirator so that it is drawn in through the aspiration hole at the distal end of the spallation tip together with the intraocularly supplied irrigating fluid and thereafter drained to the outside of the eyeball. A peristaltic pump is known as the aspirator which imparts the aspirating pressure.

As shown in FIG. 4, a peristaltic pump comprises a plurality of rollers 21' spaced apart on the same circumference of a rotating support 22' which revolves to cause the rollers 21' to compress an aspirating tube 16' to collapse on a tube receptacle 25' as they rotate. As a consequence, the fluid (aspirated liquid or air) flowing through the tube 16' is pushed out in the direction of rotation of the rollers 21', thereby creating an aspirating pressure.

A problem with the peristaltic pump shown in FIG. 4 is that when the rollers 21' start to compress the aspirating tube 16' to collapse, a portion of the fluid in the aspirating tube 16' (as indicated by volume A') will flow back. This produces periodic fluctuations in aspiration called "pulsation" which, in turn, causes pressure variations in the eye under operation, occasionally making it difficult to achieve correct control in the aspirating pressure and the rate of inflow.

SUMMARY OF THE INVENTION

The present invention has been accomplished under these circumstances and has as an object providing an irrigation-aspiration apparatus which is capable of suppressing the pulsation from aspiration to thereby secure a stable rate of inflow.

To attain this object, the present invention provides the following.

(1) An irrigation-aspiration apparatus which supplies an irrigating fluid from an irrigation container to the eye under operation and which sucks in the supplied irrigating fluid through a flexible aspirating tube together with the residue in the eye, characterized by comprising a peristaltic pump which sucks in the liquefied residue in the eye by means of rollers which compress said aspirating tube to collapse as they rotate and flattening means which flattens said aspirating tube while securing the aspirating path in said tube just prior to the point where said rollers start compressing said aspirating tube to collapse.

(2) The irrigation-aspiration apparatus of (1), wherein said aspirating tube is connected to an operation handpiece and said flattening means secures an inside dimension in the flattening direction which is at least as large as the aspiration hole in said operation handpiece.

(3) The irrigation-aspiration apparatus of (1), wherein said flattening means comprises a flattening block, a tube receptacle provided in a face-to-face relationship with said block and moving means which moves said tube receptacle and fixes it in a specified position.

BRIEF DESCRIPTION OF THE DRAWINGS

In the accompanying drawings.

Each of FIGS. 3(a) and 3(b) is an illustration of the peristaltic pump used in the apparatus shown in FIG. 1.

DETAILED DESCRIPTION OF THE PREFERRED EMBODIMENTS

Figure 1:
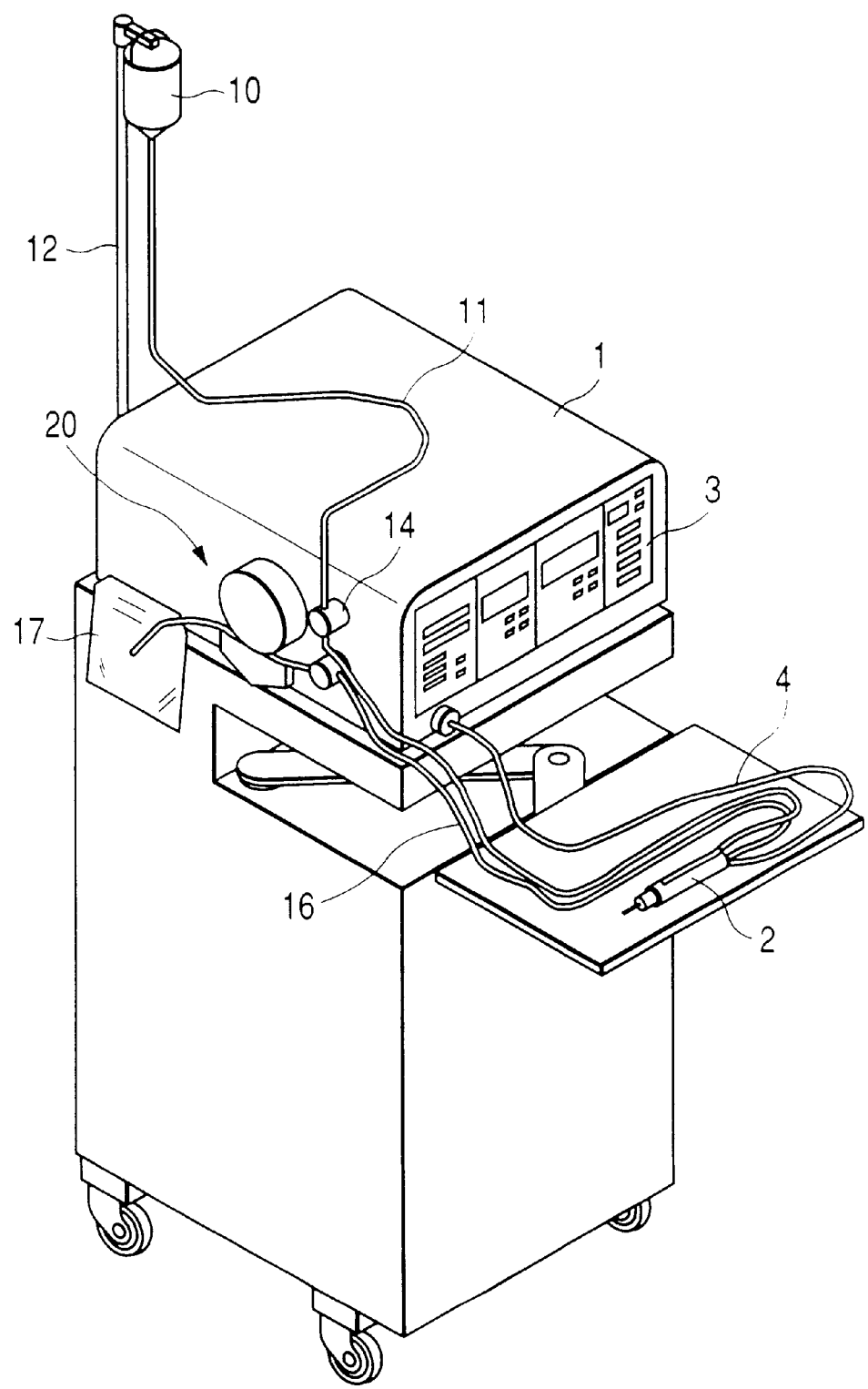
FIG. 1 is a simplified view showing the exterior appearance of an irrigation-aspiration apparatus according to an embodiment of the invention.
Figure 2:
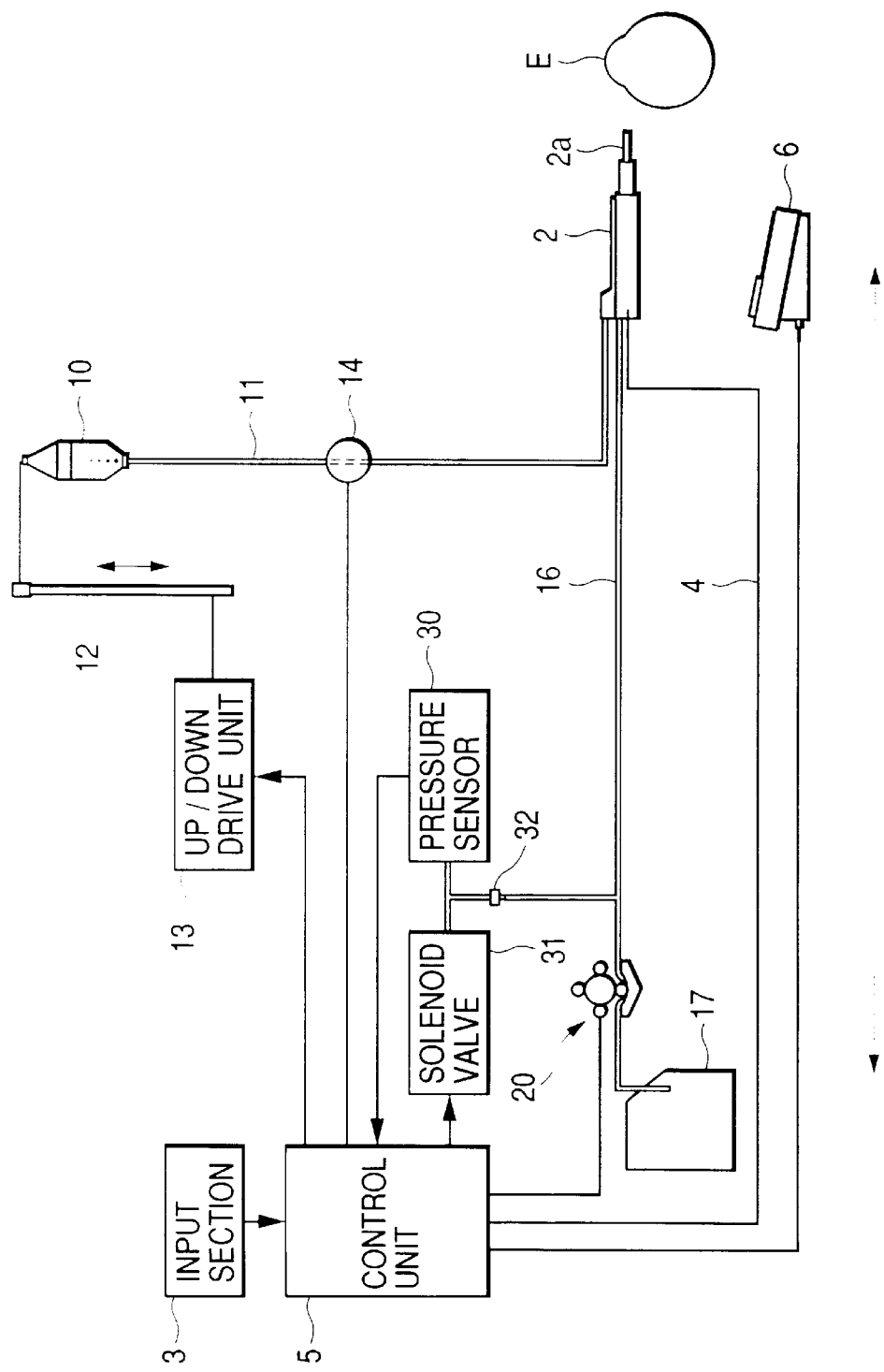
FIG. 2 shows schematically the composition of the irrigation-aspiration apparatus.

An embodiment of the invention will now be described with reference to accompanying drawings. FIG. 1 is a simplified view showing the exterior appearance of an irrigation-aspiration apparatus of the embodiment and FIG. 2 shows schematically the composition of the irrigation-aspiration apparatus.

Shown by 1 is the main body of the irrigation-aspiration apparatus of the embodiment under consideration; 2 is an US handpiece to be held by the operator. Attached to the distal end of the US handpiece 2 is a tubular spallation tip 2a having an aspiration hole which, when supplied with ultrasonic vibrations, spalls and emulsifies the nucleus in the lens of the patient's eye. Indicated by 3 is an operating panel from which the various settings of parameters such as irrigating and aspirating pressures are entered. Power for producing ultrasonic vibrations at the spallation tip 2a of the US handpiece 2 is supplied via a cable 4. The main body 1 accommodates a control unit 5 which performs overall control of the apparatus.

Reference numeral 10 designates an irrigating bottle filled with an irrigating fluid such as physiological saline to be supplied to the patient's eye E through an irrigating tube 11. The bottle 10 hangs on a pole 12 which is vertically movable by means an up/down drive unit 13 (or manually) to adjust the height of the bottle 10. The height of the bottle 10 is so set as to maintain an appropriate pressure in the patient's eye E. A control valve 14 is provided midway of the irrigating tube 11 and opened or closed to control the outflow of the irrigating fluid. An end of the irrigating tube 11 is connected to the irrigating bottle 10 and the other end to the US handpiece 2. Depending on factors such as the stage of a surgical operation and its technique, the US handpiece 2 may be replaced by an irrigating/aspirating handpiece and various other handpieces that are selectively used through reattachment.

Reference numeral 16 designates a flexible aspirating tube through which the spent irrigating fluid and liquefied residue such as the spalled and emulsified nucleus are drained from the eye as they are drawn out through the aspiration hole in the spallation tip 2a at the US handpiece 2. Provided midway of the rearward section of the aspirating tube 16 is a peristaltic suction pump unit 20 for creating the aspirating pressure (details of the suction pump unit 20 will be given below). The suction pump unit 20 is controlled by the control unit 5 such as to adjust the rate of inflow. The aspirated liquefied residue is drained into a waste bag 17.

Indicated by 30 is a pressure sensor and 31 is a solenoid valve. The pressure sensor 30 and the solenoid valve 31 are both connected to the aspirating tube 16 via a connector 32. The pressure sensor 30 normally detects the aspirating pressure. If the nucleus in the cataractal lens and the like obstruct the aspiration hole in the spallation tip 2a to increase the aspirating pressure in the aspirating tube 16 until it reaches the limit setting, the pressure sensor 30 issues a detection signal, upon which the control unit 5 turns off the suction pump 20 and thereafter maintains the limit setting of the pressure in the aspirating tube 16. If necessary, the solenoid valve 31 is opened to lower the aspirating pressure.

Shown by 6 is a foot switch and in response to various signals indicative of its selective positions, the control unit 5 controls the drive of the respective parts of the apparatus. If the US handpiece 2 is to be used, the foot switch 6 has three positions to select either an irrigation mode (performing only irrigation) or an irrigation/aspiration mode (performing both irrigation and aspiration) or an irrigation/aspiration/spallation mode (performing irrigation, aspiration and ultrasonic spallation).

Figure 3A:
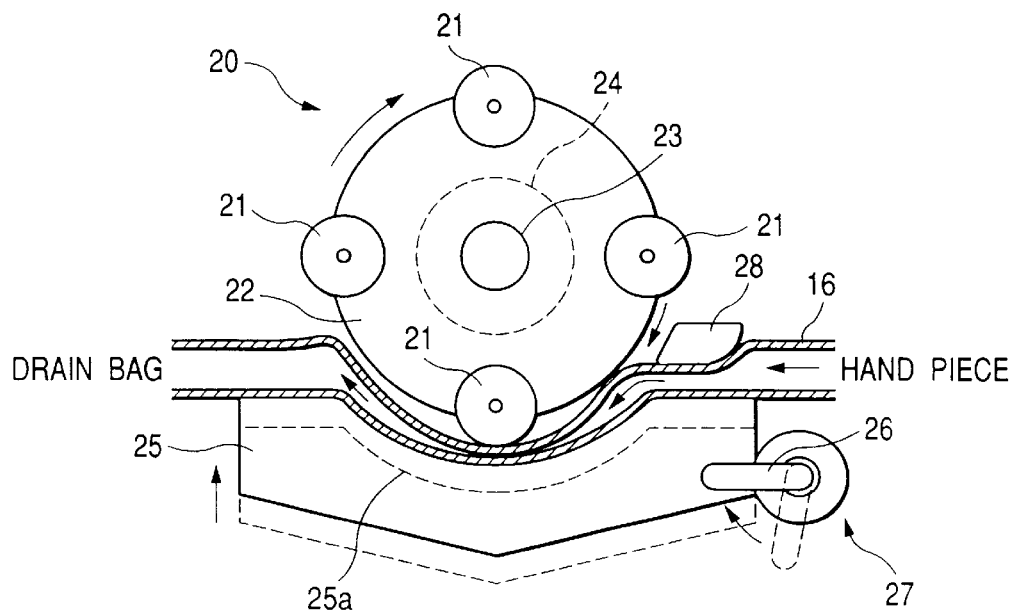
Figure 3B:
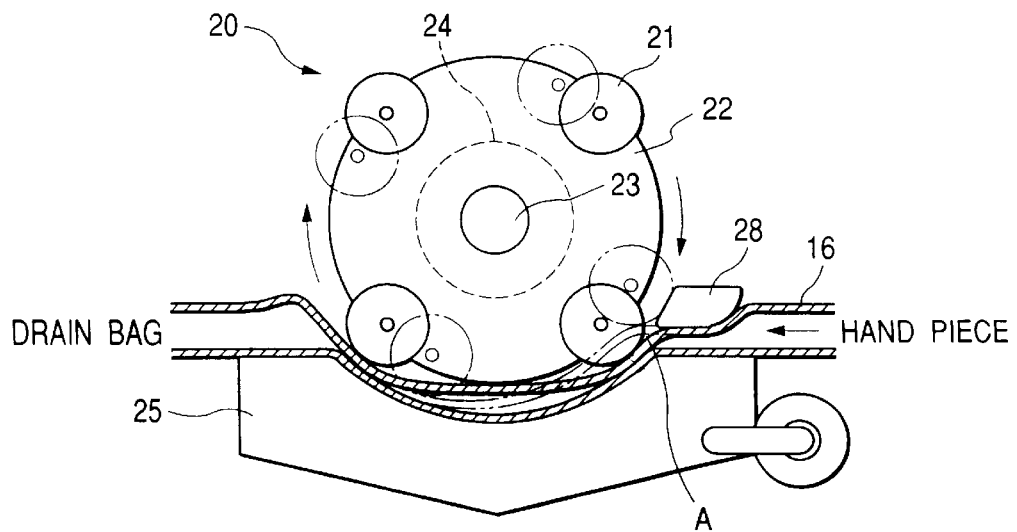

We now describe the construction of the suction pump unit 20 with reference to FIGS. 3(a) and 3(b). Indicated by 21 are rollers for compressing the aspirating tube 16 which are rotatably spaced apart at equal distance on the same circumference of a rotating support 22. The support 22 is rotated about a shaft 23 by means of a motor 24 at its back. Reference numeral 25 is a tube receptacle (platen) having an arcuate surface 25a which is vertically movable by means of an up/down mechanism 27 having a lever 26. If the lever 26 is pivoted clockwise as indicated by the arrow in FIG. 3(a), the tube receptacle 25 rises to be fixed in such a position that the aspirating tube 16 held between rollers 21 and the arcuate surface 25a is compressed to collapse with no clearance left. The arcuate surface 25a is configured such that when the tube receptacle 25 rises to be fixed in position, it forms a sector of a circle having the center at the shaft 23. The extent of the arcuate surface 25a is preferably such that at least one of the rollers 21 always compresses the aspirating tube 16 to collapse (see FIG. 3(b)). When the rotating support 22 revolves, the rollers 21 compress the aspirating tube 16 to collapse as they rotate. The rollers 21 rotate periodically, whereupon the fluid in the aspirating tube 16 is pushed forward in the direction in which the rollers 21 rotate, thereby imparting the aspirating pressure.

Shown by 28 is a block for flattening the aspirating tube 16. The block 28 projects from a side plate of the main body 1 and is located in a position just before the point where the rollers 21 start to compressing the aspirating tube 16 to collapse (i.e., just before the locus of the rotation of the outer circumference of each roller 21). If the tube receptacle 25 is elevated and fixed in position, the part of the aspirating tube 16 which is held between the flattening block 28 and the tube receptacle 25 is flattened. The clearance between the flattening block 28 and the tube receptacle 25 is so set as to secure fluid passage through the flattened aspirating tube 16. The bore size of the flattened tube as measured in the flattening direction is preferably equal to or greater than the inside diameter of the handpiece 2 in order to ensure that nuclear particles and the like passing through the aspiration hole will not be lodged in the flattened fluid channel.

Having described the construction of the irrigation-aspiration apparatus of the invention, we now explain its operation for the case where it is used in a surgical operation on a cataract by the ultrasonic phacoemulsification and aspiration technique using the US handpiece 2.

Before starting the operation, set the irrigating bottle 10, attach tubes to the US handpiece 2 and the suction pump unit 20 and make any other necessary preparations. In accordance with the setting of the irrigating pressure entered from the operating panel 3, the control unit 5 performs drive control on the up/down drive unit 13 so that the pole 12 is moved up or down to position the irrigating bottle 10 at the appropriate height (if the up/down drive unit 13 is manually operated, the irrigating bottle 10 is also adjusted in height manually).

After the necessary setting for the apparatus has ended, start the operation by the ultrasonic phacoemulsification and aspiration technique. While examining the patient's eye E with an operation microscope (not shown), the surgeon incises the sclera and the anterior capsule and inserts the spallation tip 2a at the US handpiece 2 into the eye E through the incision wound. To do this, the foot switch 6 is stepped on to the position for "irrigation mode" and the control valve 14 is opened to have the irrigating fluid flow out. When the irrigating fluid is supplied into the eye E, the anterior chamber pressure of the eyeball is maintained at an essentially constant level that is determined by the relationship with the height of the irrigating bottle 10.

To effect aspiration, the foot switch 6 is stepped on to the position for "irrigation/aspiration mode". A signal from the foot switch 6 is fed to the control unit 5, which then drives the rotating motor 24 to rotate the support 22. The rollers 21 periodically compress the aspirating tube 16 to collapse as they rotate, thereby creating the aspirating pressure in the tube 16. The aspirating pressure created by the suction pump 20 passes through the tube 16 to reach the US handpiece 2, whereupon the liquefied residue in the eye E is sucked in through the aspiration hole in the spallation tip 2a.

Figure 4:
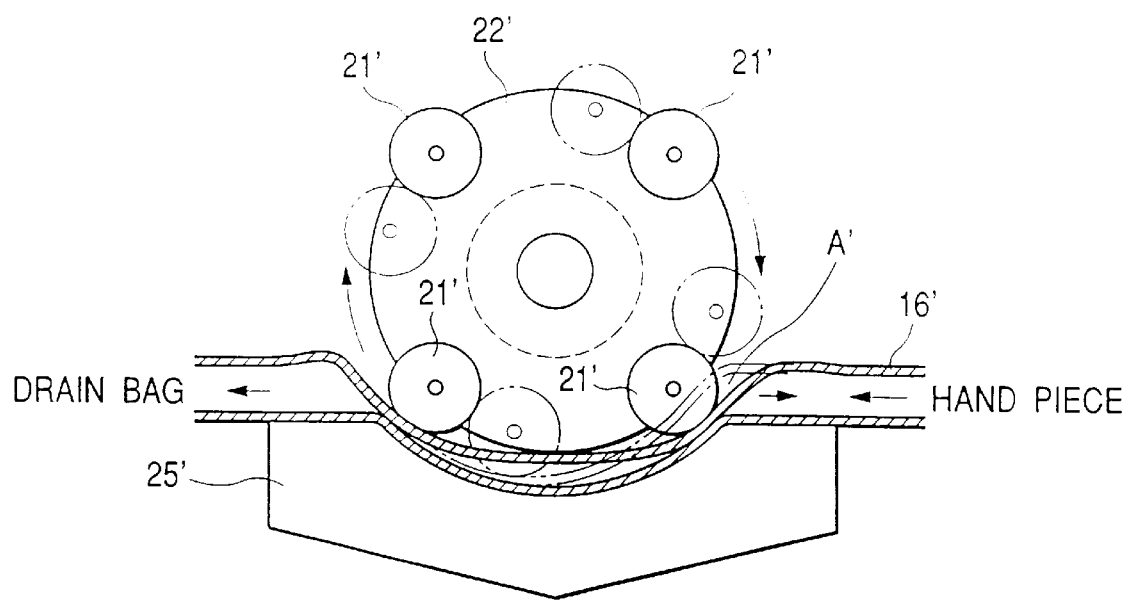
FIG. 4 is an illustration of an exemplified peristaltic pump according to the prior art.

In the invention, the aspirating tube 16 is flattened just before the rotating rollers 21 start compressing the tube 16 to collapse (just before the rotating support 22), so the change in the capacity of the tube 16 which occurs when the rollers 21 compress the tube 16 to collapse and which is indicated by A in FIG. 3(b) is smaller than the change indicated by A' in FIG. 4 and, hence, only a small volume of the liquefied residue in the tube 16 will flow back. As a consequence, the occurrence of pulsation and the resulting instability in the rate of inflow can be reduced. In addition, the signal detection by the pressure sensor 30 is sufficiently stabilized to achieve correct control of the aspirating pressure.

While the foregoing embodiment assumes the use of the US handpiece, it should be mentioned that the adverse effects of pulsation can be suppressed even if an irrigating/aspirating handpiece rather than the US handpiece is used.

The present invention permits various modifications which are encompassed by it as long as they are technologically the same in concept.

As described on the foregoing pages, the present invention is capable of reducing the pulsation from aspiration and, hence, the variations in the pressure in the eye under operation. In addition, the rate of inflow and the aspirating pressure can be sufficiently stabilized to provide ease in performing the correct control on these factors.

What is claimed is:

1. An irrigation-apparatus for use in eye surgery which sucks in supplied irrigating fluid together with a residue in an eye undergoing surgery, the irrigating fluid together with the residue defined as a liquefied residue, said aspirating apparatus comprising:

a flexible aspirating tube through which the liquefied residue is sucked;

a peristaltic pump which has a plurality of rollers and a tube receptacle and which sucks in the liquefied residue in the eye by generating aspirating pressure in said aspirating tube by rotating said rollers to compress said aspirating tube to collapse against said tube receptacle as said rollers rotate; and flattening means for flattening a portion of said aspirating tube while securing an aspirating path through said flattened portion in said aspirating tube to allow the liquefied residue to be sucked through said flattened portion during operation of said peristaltic pump, said flattening means disposed near a point where each of said rollers and said tube receptacle start compressing said aspirating tube to collapse; and wherein said flattening means is adapted to operate simultaneously while said aspirating tube is compressed to collapse by said rollers and said tube receptacle during operation of said peristaltic pump.

2. The irrigation-aspiration apparatus according to claim 1, further comprising an operation handpiece having an aspirating hole, wherein said aspirating tube is connected to said operation handpiece, and wherein said flattening means secures through said flattened portion a fluid path in said aspirating tube having a minimum dimension in a flattening direction of said flattened portion which is at least as large as the aspirating hole in said operation handpiece.

3. The irrigation aspiration apparatus according to claim 1, wherein said flattening means comprises a flattening block and a part of said tube receptacle, and wherein said flattening block is provided in a face-to-face relationship with said tube receptacle.

4. The irrigation-aspiration apparatus according to claim 1, further comprising:

an irrigation container from which an irrigating fluid is supplied to the eye; and an irrigating tube through which the irrigating fluid is supplied to the eye.

5. The irrigation-aspiration apparatus according to claim 1, wherein said peristaltic pump has a support rotatable about a shaft, and wherein each of said rollers is arranged on said support at a constant angular interval and spaced from a center of said shaft by a same distance.

6. The irrigation-aspiration apparatus according to claim 5, wherein said flattening means is disposed near said rollers so that said flattening means contacts an outer locus of each of said rollers rotating about said shaft as said rollers rotate during operation of said peristaltic pump.

7. The irrigation-aspiration apparatus according to claim 1, wherein said flattening means is disposed near said rollers so that said flattening means contacts each of said rollers as said rollers rotate during operation of said peristaltic pump.

8. The irrigation-aspiration apparatus according to claim 3, wherein said flattening block is fixed and said tube receptacle is movable.

9. A suction pump unit adapted to be arranged on an aspirating tube and between a waste bag and a handpiece in a cataract surgery apparatus, said suction pump unit comprising:

a support rotatable about an axis;

a plurality of rollers arranged on said support at constant angular intervals, each of said rollers being spaced from said axis by a same distance;

a tube receptacle having an arcuate surface and a tube holding surface adjacent said arcuate surface; and a block adapted to be spaced from said tube holding surface by a first distance smaller than an outer diameter of an aspirating tube so as to flatten a portion of the aspirating tube while securing an aspirating path through the flattened portion of the aspirating tube to allow liquefied residue to be sucked through the flattened portion during an operation of said suction pump unit, said block arranged at a position near a point where each of said rollers and said tube receptacle are adapted to start compressing the aspirating tube to collapse so as to narrow an aspirating path in the aspirating tube as a liquefied residue is sucked through the aspirating tube by operation of said suction pump unit; and wherein said block is disposed near said rollers so that said block contacts with each of said rollers as said rollers rotate pass said block.

10. The apparatus according to claim 9, wherein said block is movable between a first position wherein said block is spaced from said tube holding surface by said first distance and a second position wherein said block is spaced from said tube holding surface by a second distance larger than said first distance.

11. The apparatus according to claim 9, wherein a minimal distance between each of said rollers and said arcuate surface is smaller than said first distance.

12. The apparatus according to claim 9, wherein said tube receptacle is movable between a first position wherein said tube holding surface is spaced from said block by said first distance and a second position wherein said tube holding surface is spaced from said block by a second distance larger than said first distance.

13. An irrigation-aspiration apparatus for use in eye surgery which sucks in supplied irrigating fluid together with a residue in an eye undergoing surgery, the irrigating fluid together with the residue defined as a liquefied residue, said aspirating apparatus comprising:

a flexible aspirating tube through which the liquefied residue is sucked;

a peristaltic pump which has a plurality of rollers and a tube receptacle and which sucks in the liquefied residue in the eye by generating aspirating pressure in said aspirating tube by rotating said rollers to compress said aspirating tube to collapse against said tube receptacle as said rollers rotate;

flattening means for flattening a portion of said aspirating tube while securing an aspirating path through said flattened portion in said aspirating tube to allow the liquefied residue to be sucked through said flattened portion during operation of said peristaltic pump, said flattening means disposed near a point where each of said rollers and said tube receptacle start compressing said aspirating tube to collapse;

wherein said flattening means comprises a flattening block and a part of said tube receptacle, and wherein said flattening block is provided in a face-to-face relationship with said tube receptacle; and said irrigation-aspiration apparatus further comprising means for moving said tube receptacle to a predetermined position and fixing said tube receptacle at said predetermined position so as to compress said aspirating tube to collapse by engagement with said rollers during operation of said peristaltic pump and so as to flatten the portion of said aspirating tube with said flattening block.

14. An irrigation-aspiration apparatus for use in eye surgery which sucks in supplied irrigating fluid together with a residue in an eye undergoing surgery, the irrigating fluid together with the residue defined as a liquefied residue, said aspirating apparatus comprising:

a flexible aspirating tube through which the liquefied residue is sucked;

a peristaltic pump which has a plurality of rollers and a tube receptacle and which sucks in the liquefied residue in the eye by generating aspirating pressure in said aspirating tube by rotating said rollers to compress said aspirating tube to collapse against said tube receptacle as said rollers rotate;

flattening means for flattening a portion of said aspirating tube while securing an aspirating path through said flattened portion in said aspirating tube to allow the liquefied residue to be sucked through said flattened portion during operation of said peristaltic pump, said flattening means disposed near a point where each of said rollers and said tube receptacle start compressing said aspirating tube to collapse;

wherein said peristaltic pump has a support rotatable about a shaft, and wherein each of said rollers is arranged on said support at a constant angular interval and spaced from a center of said shaft by a same distance; and wherein said flattening means is disposed near said rollers so that said flattening means contacts an outer locus of each of said rollers rotating about said shaft as said rollers rotate during operation of said peristaltic pump.

15. An irrigation-aspiration apparatus for use in eye surgery which sucks in supplied irrigating fluid together with a residue in an eye undergoing surgery, the irrigating fluid together with the residue defined as a liquefied residue, said aspirating apparatus comprising:

a flexible aspirating tube through which the liquefied residue is sucked;

a peristaltic pump which has a plurality of rollers and a tube receptacle and which sucks in the liquefied residue in the eye by generating aspirating pressure in said aspirating tube by rotating said rollers to compress said aspirating tube to collapse against said tube receptacle as said rollers rotate;

flattening means for flattening a portion of said aspirating tube while securing an aspirating path through said flattened portion in said aspirating tube to allow the liquefied residue to be sucked through said flattened portion during operation of said peristaltic pump, said flattening means disposed near a point where each of said rollers and said tube receptacle start compressing said aspirating tube to collapse; and wherein said flattening means is disposed near said rollers so that said flattening means contacts each of said rollers as said rollers rotate during operation of said peristaltic pump.

* * * * *